United States Patent [19]

Sterzer

[11] Patent Number: 5,098,429
[45] Date of Patent: Mar. 24, 1992

[54] ANGIOPLASTIC TECHNIQUE EMPLOYING AN INDUCTIVELY-HEATED FERRITE MATERIAL

[75] Inventor: Fred Sterzer, Princeton, N.J.

[73] Assignee: MMTC, Inc., Princeton, N.J.

[21] Appl. No.: 510,085

[22] Filed: Apr. 17, 1990

[51] Int. Cl.[5] .......................................... A61B 17/38
[52] U.S. Cl. ..................................... 606/28; 128/401; 128/804
[58] Field of Search .................. 606/28, 31; 128/401, 128/804

[56] References Cited

U.S. PATENT DOCUMENTS

| | | | |
|---|---|---|---|
| 4,643,186 | 2/1987 | Rosen et al. | 128/804 |
| 4,654,024 | 3/1987 | Crittenden et al. | 606/28 |
| 4,672,962 | 6/1987 | Hershenson | 128/401 |
| 4,773,413 | 9/1988 | Hussein et al. | 606/28 |
| 4,790,311 | 12/1988 | Ruiz | 606/28 |
| 4,799,479 | 1/1989 | Spears | 606/28 |
| 4,807,620 | 2/1989 | Strul et al. | 606/28 |
| 4,955,377 | 9/1990 | Lennox et al. | 128/401 |
| 5,035,694 | 7/1991 | Kasprzyk et al. | 606/28 |
| 5,045,056 | 9/1991 | Behl | 128/401 |
| 5,047,025 | 9/1991 | Taylor et al. | 606/28 |

FOREIGN PATENT DOCUMENTS

| | | | |
|---|---|---|---|
| 0222137 | 5/1987 | European Pat. Off. | 606/28 |
| 0315730 | 5/1989 | European Pat. Off. | 128/401 |
| 3725691 | 3/1988 | Fed. Rep. of Germany | 128/401 |
| 2052663 | 2/1990 | Japan | 606/28 |
| 2057264 | 2/1990 | Japan | 606/28 |

*Primary Examiner*—Lee S. Cohen
*Assistant Examiner*—Krista Pfaffle
*Attorney, Agent, or Firm*—George J. Seligsohn

[57] ABSTRACT

Disclosed are three forms of an angioplastic instrument employing a ferrite material inductively-heated from outside a patient's body to soften plaque occluding a lumen of a vas of the patient. In a first form, the angioplastic instrument is comprised solely of a thin guide wire having a ferrite-coated tip at its distal end. Each of the other two forms of the angioplastic instrument heats the liquid filling the balloon of an angioplastic balloon catheter with the inductively-heated ferrite material. By utilizing ferrite materials having different Curie temperatures, the amount of heating can be adjusted for a particular treatment protocol. Also, by limiting the value of the Curie temperature of the ferrite material to a safe value, the tissue underlying the vas is inherently protected from undue injury due to overheating.

12 Claims, 3 Drawing Sheets

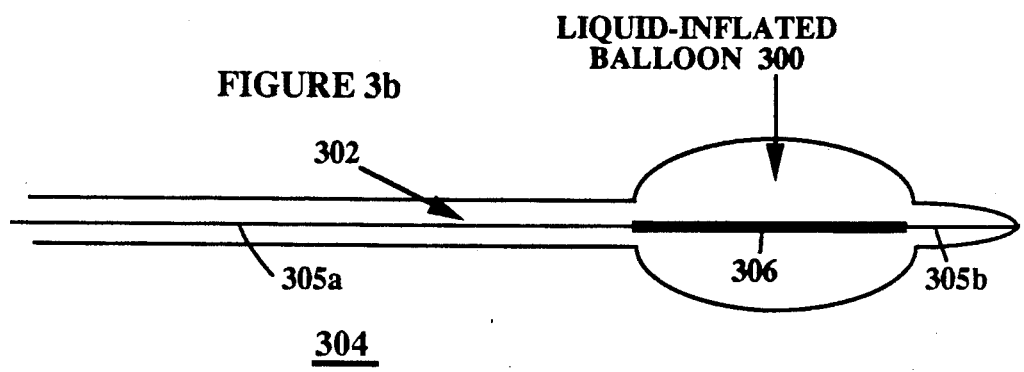
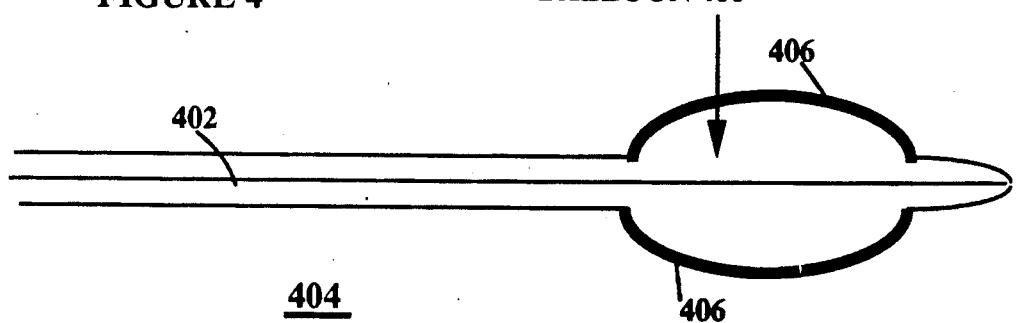

ANGIOPLASTIC TECHNIQUE EMPLOYING AN INDUCTIVELY-HEATED FERRITE MATERIAL

BACKGROUND OF THE INVENTION

An angioplastic technique employing balloon catheters is known in the art. Such a technique involves threading a catheter arrangement, including a thin guide wire (which may have a diameter of only about 20 mils) and a deflated balloon located toward the distal end of the catheter, through the vascular system of a patient's body until the balloon is situated within the bore of the lumen of a vas, such as a coronary artery, that is partially occluded with atherosclerotic plaque. The balloon is then inflated with a liquid, which causes the inflated balloon to press against the plaque (which is usually comprised of a fatty substance, but which may to some extent be calcified). In any case, the pressure of the inflated balloon against the plaque of the partially occluded lumen deforms the plaque and the walls of the vas, thereby enlarging the bore of the lumen.

It has been found that the fatty substance of the plaque may be softened and that the walls of the vas may be stiffened by heating the plaque to a given temperature. While this given temperature has to be sufficiently high to result in the desired softening and stiffening, it must not become so high as to unduly injure the underlying tissue of the vas. In this regard, reference is made to U.S. Pat. No. 4,643,186, which issued to Rosen et al. on Feb. 17, 1987. This Rosen et al. patent discloses the use of microwave energy to provide the desired heating of the plaque and the walls of the vas. The microwave energy is radiated from an antenna situated toward the distal end of the catheter. The radiated microwave energy may directly dielectrically heat the plaque and the walls of the vas and/or the radiated microwave energy may dielectrically heat the liquid inflating the balloon which, in turn, heats the plaque and the walls of the vas by conduction of heat therefrom through the balloon.

Further, it has been found that a portion of the fatty substance of the plaque under such heat and pressure tends to liquify and rise to the surface of the plaque. In this regard, reference is made to my allowed U.S. patent application Ser. No. 07/190,179, filed May 4, 1988. This application discloses sucking out, through the catheter, the liquified fatty substance of the plaque produced by the pressure thereagainst by an inflated balloon and the direct and/or indirect heating thereof by radiated energy from an antenna situated toward the distal end or the catheter.

There are problems associated with heating the plaque by means of radiated energy from an antenna situated toward the distal end of a balloon catheter. Such a catheter requires a transmission line extending the length of the catheter for energizing the antenna. Further, in order to avoid undue injury to the underlying vas tissue by overheating beyond a safe desired temperature, a temperature sensing element must also be situated toward the distal end of the catheter, and the output of such temperature sensing element must be transmitted to an energy control device situated outside of the patient's body by means of wires extending the length of the catheter. The presence of the antenna, transmission line, temperature sensing element and wires limits the minimum size of the diameter of the catheter. Therefore, such a catheter cannot be inserted into small veins or arteries or into a larger vas in which the thickness of the plaque occluding the lumen thereof is so great to make the original bore of this occluded lumen too small to fit the diameter of the catheter. Furthermore, no type of balloon catheter can be used to open or enlarge a completely or a substantially completely occluded lumen of a vas.

SUMMARY OF THE INVENTION

The angioplastic technique of the present invention solves the aforesaid problems by inductively heating ferrite material situated within a vas of a patient's body in the vicinity of plaque occluding the lumen of the vas with energy radiated from outside the patient's body to the ferrite material situated within the vas. The inductive heating of the ferrite material results primarily from induced excursions around the hysteresis loop thereof, rather than from induced eddy currents therein.

More specifically, the angioplastic technique of the present invention involves heating plaque occluding the lumen of a vas of a patient's body to a first temperature which is sufficiently high to soften the plaque to a given extent and/or cause stiffening of the walls of the vas. This is accomplished by placing a ferrite material within the vas in the vicinity of the plaque, and irradiating the ferrite material from outside the patient's body with sufficient radiated energy to inductively heat the ferrite material to a second temperature which is at least as high as the first temperature. The heat from the heated ferrite material is then transmitted to the plaque for a sufficient time to effect the heating of the plaque to the first temperature.

An advantage of the present invention is that a ferrite material has a Curie temperature, determined by its particular formulation, above which it cannot be heated by induced hysteresis to any appreciable extent by excess radiation energy impinging thereon. Therefore, by employing a ferrite material formulation having a Curie temperature which does not exceed a safe temperature to prevent undue injury to the underlying vas tissue, the need for a temperature sensing element and its connecting wires within the vas is done away with.

BRIEF DESCRIPTION OF THE DRAWING

FIG. 4 illustrates an angioplastic balloon catheter arrangement in which the balloon itself is coated with ferrite material.

DESCRIPTION OF THE PREFERRED EMBODIMENTS

Figure 1:
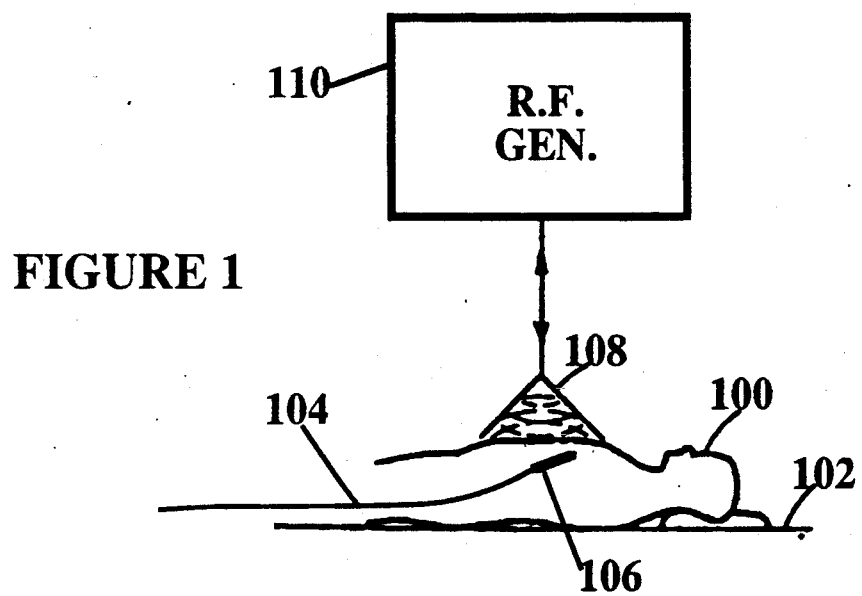
FIG. 1 is a diagrammatic showing of a patient being treated in accordance with the angioplastic technique of the present invention.

Referring to FIG. 1, patient 100, lying on table 102, is undergoing treatment in accordance with the angioplastic technique of the present invention. Specifically, an angioplastic instrument 104 (which may take the form shown in any one of FIGS. 2, 3b or 4, described in detail below) is threaded through the vascular system of patient 100, with the distal end thereof being positioned in the vicinity of the plaque occluding the lumen of the vas to be treated (assumed for illustrative purposes to be a coronary artery). In all cases, angioplastic instrument 104 includes ferrite material 106 located towards its distal end and positioned in cooperative relationship with the plaque occluding the lumen so that heating of ferrite material 106 to this plaque.

Radiator 108, situated outside of the body of patient 100 and energized by the output of radio-frequency (R.F.) generator 110, irradiates the chest of patient 100 with R.F. energy, as shown. The frequency value of this R.F. energy preferably should be sufficiently high to efficiently hysteresis-heat (i.e. be readily absorbed by) ferrite material on which it impinges, but sufficiently low to only negligibly dielectrically heat body tissue through which it passes (i.e. body tissue be relatively transparent to such a value of R.F. frequency). An R.F. frequency value in the range of 50 kHz. fulfills these criteria.

More particularly, absorbed R.F. energy is effective in inductively heating ferrite material 106 both by inducing excursions around its hysteresis loop and by inducing eddy currents therein. However, the induced eddy currents are relatively small and are insufficient by themselves to maintain ferrite material 106 at its Curie temperature. Therefore, when hysteresis-heating of ferrite material 106 ceases upon reaching its Curie temperature, eddy-current-heating thereof, which continues, cannot cause the temperature of ferrite material 106 to rise significantly above its Curie temperature (i.e., the transmission of heat away from ferrite material 106 at its Curie temperature is greater than the heat being added by the induced eddy currents).

Ferrite material 106, which is hysteresis-heated by radiation from radiator 108 which reaches it after passing through body tissue of patient 100, reaches a temperature sufficiently high to effect the desired softening of the plaque with which it is positioned in cooperative relationship by heat transmitted therefrom to such plaque (softening of the plaque normally occurs at temperatures of 45° C. or higher). However, as discussed above, the Curie temperature of the heated ferrite material 106 should be sufficiently low to prevent the undesired occurrence of undue injury to the vas tissue underlying such plaque. In this regard, there is a difference of opinion in medical circles as to whether or not minor injury to the underlying vas tissue to effect a stiffening thereof is desirable. If so, only injury beyond such minor injury should be considered as undue injury. Otherwise, any injury at all may be considered as undue injury.

Injury to tissue depends both on the temperature value to which the tissue is heated, the type of tissue being heated, and the time duration that this temperature value persists. Experimental evidence shows that tissue heated to a temperature above some value between about 65° C. and somewhat over 70° C., depending on the type of tissue, for even several seconds undergoes injury. However, tissue can be heated to a value of somewhat more than 40° C. for an indefinite period. Angina or even a heart attack is likely to be induced by a partially-occluded coronary artery being blocked by the inflated balloon of an angioplastic catheter for more than a certain time (e.g., about a minute). Therefore, in such cases, the temperature to which the liquid within the inflated balloon is heated by hysteresis-heated ferrite material 106 must be sufficiently high so that the conduction of heat therefrom into the occluding plaque sufficient to soften the plaque is accomplished within a maximum period of well below a minute, without the transmission of the heat through the thickness of the plaque to the underlying tissue of the vas being sufficient to raise this tissue to a temperature value which persists for a sufficient time to unduly injury this tissue. A ferrite Curie temperature, corresponding to a typical maximum operating temperature for inductively-heated ferrite material 106, which satisfies these conditions is about 70° C.

In the case in which the vas lumen is completely occluded, a longer heating period at a lower maximum-operating temperature (i.e., ferrite material 106 may have a lower Curie temperature) often can be employed. This is desirable in the case in which the lumen of a larger vas is completely or substantially completely occluded by thick plaque. However, in the case in which the lumen of a small vas is completely or substantially completely occluded, so that the plaque separating the ferrite material 106 from the underlying vas tissue may be thin, it may be desirable to employ a higher maximum-operating temperature for a shorter period of time in order to soften the plaque without undue injury to the underlying vas tissue. In this latter case, a ferrite material 106 having a Curie temperature of about 80° C.–100° C. may be employed.

Figure 2:
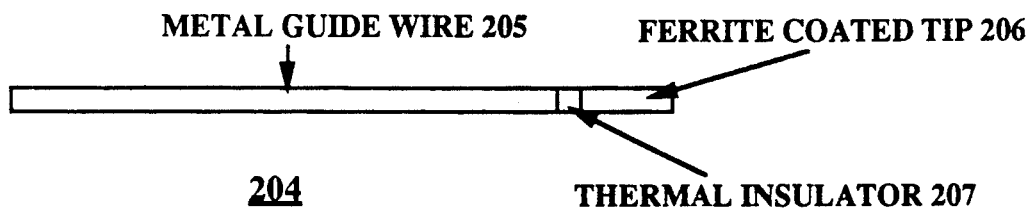
FIG. 2 illustrates a first embodiment of a guide wire comprised of ferrite material, which is useful by itself as an angioplastic instrument.

Reference is now made to FIG. 2, which shows a complete angioplastic instrument 204. Angioplastic instrument 204, which constitutes a first form that angioplastic instrument 104 of FIG. 1 may take, is comprised of a metal guide wire 205 having a ferrite-coated tip 206 at its distal end, which, as shown, is separated from the rest of metal guide wire 205 by thermal insulator 207. The respective diameters of metal guide wire 205, ferrite-coated tip 206 and thermal insulator 207 of angioplastic instrument 204, are all quite small (typically about 20 mils). Therefore, angioplastic instrument 204 can enter the non-occluded bore of a lumen which is too small for a balloon catheter to enter (either because the diameter of the entered vas itself is too small or because the plaque occluding the lumen is so thick as to make the non-occluded bore thereof too small). Further, the inductively-heated ferrite-coated tip 206 of angioplastic instrument 204 can be used to open up a lumen of a vas which is completely or substantially completely occluded by plaque. In those cases in which the diameter of a completely-occluded vas itself is sufficiently larger, the ferrite-coated tip 206 of angioplastic instrument 204 can be used to first open up a lumen bore of sufficient diameter to permit a balloon catheter to enter, and then a balloon catheter can be used to further enlarge the lumen bore.

Figure 3A:
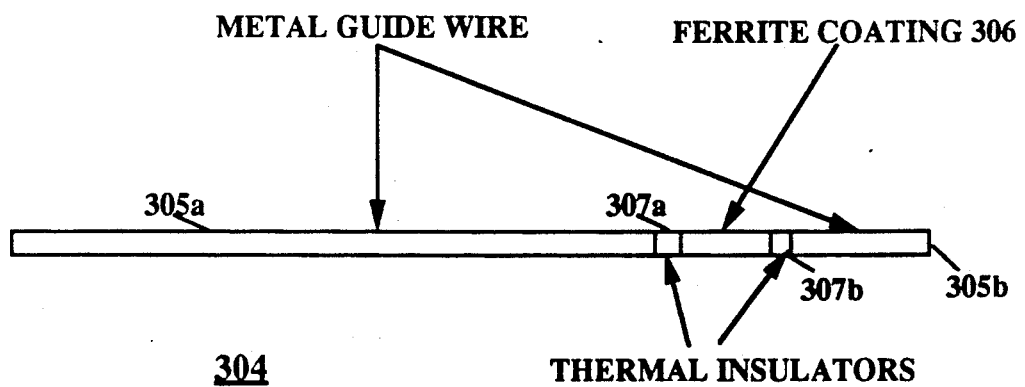
FIG. 3a illustrates a second embodiment of a guide wire comprised of ferrite material, which is useful when incorporated in the angioplastic balloon catheter arrangement shown in FIG. 3b.

Reference is now made to FIG. 3b, which shows a balloon catheter 304 which constitutes a second form that angioplastic instrument 104 of FIG. 1 may take. Specifically, catheter 304 is comprised of a conventional liquid-inflated balloon 300 and a guide wire 302, with guide wire 302 including a ferrite coating 306 disposed as shown for heating the liquid in balloon 300 in response to ferrite coating 306 itself being inductively heated. As shown in detail in FIG. 3a, guide wire 302 is made of ferrite coating 306 located near its distal end attached by a first thermal insulator 307a to a first relatively long metal wire 305a extending all the way to the proximate end of guide wire 302 and attached by a second thermal insulator 307b to a second relatively short metal wire 305b extending all the way to the distal end of guide wire 302.

Reference is now made to FIG. 4, which shows a balloon catheter 404 which constitutes a third form that angioplastic instrument 104 of FIG. 1 may take. Catheter 404 is comprised of a ferrite-coated, liquid-filled balloon 400 and a conventional guide wire 402. Ferrite-coated, liquid-filled balloon 400 differs from a conventional liquid-filled balloon of an angioplastic catheter by having the inside surface and/or outside surface of a conventional balloon coated with a ferrite material 406 (as indicated in FIG. 4 by the thickened outline of balloon 400).

In the case of the first form of angioplastic instrument 104, shown in FIG. 2, the ferrite material of hysteresis-heated ferrite-coated tip 206 of angioplastic instrument 204, is placed in direct contact with the plaque to be softened and, therefore, directly transmits heat to the plaque. However in the case of the second and third forms of angioplastic instrument 104, shown in FIGS. 2 and 3, nearly all the heat generated by hysteresis-heated ferrite-coatings 306 and 406 is used to heat the inflating liquid filling balloons 300 and 400, and the plaque is softened for the most part by heat transmitted to the plaque from this heated liquid, rather than from the ferrite coating itself.

What is claimed is:

1. In an angioplastic instrument comprising guide-wire means having a cross section and a distal end which is adapted to be threaded through the vascular system of a patient's body and be positioned in cooperative relationship with plaque occluding the lumen of a vas having a cross section no smaller in size than that of the cross section of said guide-wire means; wherein said guide-wire means includes ferrite material situated toward said distal end thereof; the improvement wherein:
   said ferrite material is isolated from and electrically floats with respect to points of potential outside of said patient's body, thereby permitting the size of said cross section of said guide-wire means to be reduced;
   whereby said ferrite material is inductively heated solely by radio-frequency radiation that has been transmitted thereto from outside of said patient's body and absorbed thereby.

2. The angioplastic instrument defined in claim 1, wherein:
   said ferrite material is a material that exhibits a given Curie temperature characterized by a loss of ability of said ferrite material to convert said radio-frequency radiation into heat at a maximum temperature equal to said given Curie temperature.

3. The angioplastic instrument defined in claim 1, wherein:
   said guide-wire means comprises a guide wire having an exposed tip situated substantially at said distal end of said guide-wire means, whereby said exposed tip may be placed in direct contact with said plaque occluding the lumen of said vas; and
   said exposed tip of said guide wire including said ferrite material.

4. The angioplastic instrument defined in claim 3, wherein:
   said guide wire includes a thermal insulator having two ends, one of said two ends of said thermal insulator being attached to said exposed tip of said guide wire, and said guide wire further includes a remainder portion thereof adapted to be threaded through the vascular system of said patient's body that is attached to the other of said two ends of said thermal insulator.

5. The angioplastic instrument defined in claim 3, wherein:
   said guide-wire means consists of said guide wire.

6. The angioplastic instrument defined in claim 5, wherein:
   at least said distal end of said guide wire has a cross-section of substantially 20 mils.

7. The angioplastic instrument defined in claim 1, wherein:
   said guide-wire means comprises a guide wire having an exposed tip situated substantially at said distal end of said guide-wire means, whereby said exposed tip may be placed in direct contact with said plaque occluding the lumen of said vas; and
   said exposed tip of said guide wire is coated with said ferrite material.

8. The angioplastic instrument defined in claim 1, wherein:
   said guide-wire means comprises a guide wire and a catheter surrounding said guide wire, said catheter having a liquid-inflatable balloon situated toward said distal end of said guide-wire means, said balloon being located in cooperative relationship with said ferrite material so that inductive-heating of said ferrite material while said balloon is inflated results in the heating of liquid filling said balloon.

9. The angioplastic instrument defined in claim 8, wherein:
   a portion of said guide wire is situated within said balloon, and said portion of said guide wire comprises said ferrite material.

10. The angioplastic instrument defined in claim 9, wherein:
    said guide wire includes first and second thermal insulators, a metal terminal portion of said guide wire that extends to the tip of said distal end of said guide-wire means, and a metal remaining portion of said guide wire adapted to be threaded through the vascular system of said patient's body; and
    said first thermal insulator attaches one end of said portion of said guide wire situated within said balloon to said metal terminal portion of said guide wire, and said second thermal insulator attaches the other end of said portion of said guide wire to said metal remaining portion of said guide wire.

11. The angioplastic instrument defined in claim 8, wherein:
    a portion of said guide wire is situated within said balloon, and said portion of said guide wire is coated with said ferrite material.

12. The angioplastic instrument defined in claim 8, wherein:
    at least one surface of said balloon is coated with said ferrite material.

* * * * *